(12) United States Patent
Rasmussen et al.

(10) Patent No.: US 11,657,918 B2
(45) Date of Patent: May 23, 2023

(54) GENERATING DATA IN STANDARDIZED FORMATS AND PROVIDING RECOMMENDATIONS

(71) Applicant: Northwestern University, Evanston, IL (US)

(72) Inventors: Luke V. Rasmussen, Wilmette, IL (US); Justin B. Starren, Wilmette, IL (US); Carl Christensen, Terra Ceia, FL (US); Federico A. Almaraz, Chicago, IL (US); Maureen E. Smith, Chicago, IL (US)

(73) Assignee: Northwestern University, Evanston, IL (US)

( * ) Notice: Subject to any disclaimer, the term of this patent is extended or adjusted under 35 U.S.C. 154(b) by 369 days.

(21) Appl. No.: 16/444,742

(22) Filed: Jun. 18, 2019

(65) Prior Publication Data

US 2019/0385743 A1 Dec. 19, 2019

Related U.S. Application Data

(60) Provisional application No. 62/686,383, filed on Jun. 18, 2018.

(51) Int. Cl.
*G16H 50/20* (2018.01)
*G16B 50/00* (2019.01)
(Continued)

(52) U.S. Cl.
CPC ........... *G16H 50/20* (2018.01); *G06F 16/258* (2019.01); *G16B 50/00* (2019.02); *G16H 20/10* (2018.01)

(58) Field of Classification Search
CPC ...... G06F 16/258; G16H 50/20; G16H 15/00; G16B 20/00; G16B 25/20; C12N 2795/10211; Y02A 90/10
See application file for complete search history.

(56) References Cited

U.S. PATENT DOCUMENTS

| | | | |
|---|---|---|---|
| 2013/0110775 A1* | 5/2013 | Forsythe | G06F 16/90 707/613 |
| 2014/0222349 A1* | 8/2014 | Higgins | G16B 20/00 702/19 |
| 2014/0278478 A1* | 9/2014 | Vezina | A61B 5/0006 705/2 |

OTHER PUBLICATIONS

Bosca D, Marco L, Burriel V, Jaijo T, Millan JM, Levin A, et al. Genetic testing information standardization in HL7 CDA and ISO13606. Stud Health Technol Inform. 2013;192:338-42.
(Continued)

*Primary Examiner* — Reginald R Reyes
(74) *Attorney, Agent, or Firm* — Banner & Witcoff, Ltd.

(57) ABSTRACT

Systems and methods for integrating genomic results with electronic health records in accordance with embodiments of the invention are disclosed. In one embodiment, a method includes obtaining first raw genetic data formatted in a first format, obtaining second raw genetic data formatted in a second format normalizing the first raw genetic data by substituting at least one symbol in the first raw genetic data, normalizing the second raw genetic data, generating genetic data for the patient by modifying the first raw genetic data by converting the normalized symbols in the first raw genetic data to a common format, modifying the second raw genetic data by converting the normalized symbols in the second raw genetic data to the common format, and generating the genetic data for the patient based on the first raw genetic data and the second raw genetic data, and storing the genetic data.

20 Claims, 5 Drawing Sheets

(51) Int. Cl.
G16H 20/10 (2018.01)
G06F 16/25 (2019.01)

(56) References Cited

OTHER PUBLICATIONS

Hoffman MA. The genome-enabled electronic medical record. J Biomed Inform. Feb. 2007;40(1):44-6.
Kho AN, Rasmussen LV, Connolly JJ, Peissig PL, Starren J, Hakonarson H, et al. Practical challenges in integrating genomic data into the electronic health record. Genet Med. Oct. 2013;15(10)772-8.
Masys DR, Jarvik GP, Abernethy NF, Anderson NR, Papanicolaou GJ, Paltoo DN, et al. Technical desiderata for the integration of genomic data into Electronic Health Records. J Biomed Inform. Jun. 2012;45(3):419-22.
Herr TM, Bielinski SJ, Bottinger E, Brautbar A, Brilliant M, Chute CG, et al. A conceptual model for translating omic data into clinical action. J Pathol Inform. 2015;6:46.
Welch BM, Eilbeck K, Del Fiol G, Meyer LJ, Kawamoto K. Technical desiderata for the integration of genomic data with clinical decision support. J Biomed Inform. Oct. 2014;51:3-.
Marsolo K, Spooner SA. Clinical genomics in the world of the electronic health record. Genet Med. Oct. 2013;15(10):786-91.
Rasmussen-Torvik LJ, Stallings SC, Gordon AS, Almoguera B, Basford MA, Bielinski SJ, et al. Design and anticipated butcomes of the eMERGE-PGx project: a multicenter pilot for preemptive pharmacogenomics in electronic health record systems. Clin Pharmacol Ther. Oct. 2014;96(4):482-9.
Starren J, Williams MS, Bottinger EP. Crossing the omic chasm: a time for omic ancillary systems. Jama. Mar. 27, 2013;309(12):1237-8.
Relling MV, Klein TE. CPIC: Clinical Pharmacogenetics Implementation Consortium of the Pharmacogenomics Research Network. Clin Pharmacol Ther. Mar. 2011;89(3):464-7.
Aronson SJ, Clark EH, Babb LJ, Baxter S, Farwell LM, Funke BH, et al. The Geneinsight Suite: a platform to support laboratory and provider use of DNA-based genetic testing. Hum Mutat. May 2011;32(5):532-6.
Huang L, Fernandes H, Zia H, Tavassoli P, Rennert H, Pisapia D, et al. The cancer precision medicine knowledge base for structured clinical-grade mutations and interpretations. Journal of the American Medical Informatics Association. 2016.
Beyan T, Aydin Son Y. Incorporation of personal single nucleotide polymorphism (SNP) data into a national level electronic health record for disease risk assessment, part 2: the incorporation of SNP into the national health information system of Turkey. JMIR Med Inform. Aug. 11, 2014;2(2):e17.
Laerum H, Bremer S, Bergan S, Grunfeld T. A taste of individualized medicine: physicians' reactions to automated genetic interpretations. J Am Med Inform Assoc. Feb. 2014;21(e1):e143-6.
Hoffman JM, Haidar CE, Wilkinson MR, Crews KR, Baker DK, Kornegay NM, et al. PG4KDS: a model for the clinical implementation of pre-emptive pharmacogenetics. Am J Med Genet C Semin Med Genet. Mar. 2014;166c(1):45-55.
Hicks JK, Crews KR, Hoffman JM, Kornegay NM, Wilkinson MR, Lorier R, et al. A clinician-driven automated system for integration of pharmacogenetic interpretations into an electronic medical record. Clin Pharmacol Ther. Nov. 2012;92(5):563-6.
Bielinski SJ, Olson JE, Pathak J, Weinshilboum RM, Wang L, Lyke KJ, et al. Preemptive genotyping for personalized medicine: design of the right drug, right dose, right time-using genomic data to individualize treatment protocol. Mayo Clin Proc. Jan. 2014;89(1):25-33.
Gottesman O, Scott SA, Ellis SB, Overby CL, Ludtke A, Hulot JS, et al. The CLIPMERGE PGx Program: clinical implementation of personalized medicine through electronic health records and genomics-pharmacogenomics. Clin Pharmacol Ther. Aug. 2013;94(2):214-7.
Caraballo PJ, Bielinski SJ, St Sauver JL, Weinshilboum RM. Electronic Medical Record-Integrated Pharmacogenomics and Related Clinical Decision Support Concepts. Clin Pharmacol Ther. Aug. 2017;102(2):254 64.
Nishimura AA, Shirts BH, Dorschner MO, Amendola LM, Smith JW, Jarvik GP, et al. Development of clinical decision support alerts for pharmacogenomic incidental findings from exome sequencing. Genet Med. Nov. 2015;17(11):939-42.
Aronson SJ, Clark EH, Varugheese M, Baxter S, Babb LJ, Rehm HL. Communicating new knowledge on previously reported genetic variants. Genet Med. Apr. 5, 2012.
Wilcox AR, Neri PM, Volk LA, Newmark LP, Clark EH, Babb LJ, et al. A novel clinician interface to improve clinician access to up-to-date genetic results. J Am Med Inform Assoc. Feb. 2014;21(e1):e117-21.
Neri PM, Pollard SE, Volk LA, Newmark LP, Varugheese M, Baxter S, et al. Usability of a novel clinician interface for genetic results. J Biomed Inform. Oct. 2012;45(5):950-7.
Klinkenberg-Ramirez S, Neri PM, Volk LA, Samaha SJ, Newmark LP, Pollard S, et al. Evaluation: a Qualitative Pilot Study of Novel Information Technology Infrastructure to Communicate Genetic Variant Updates. Applied Clinical Informatics. 2016;7(2):461-76.
Overby CL, Heale B, Aronson S, Cherry JM, Dwight S, Milosavljevic A, et al. Providing Access to Genomic Variant Knowledge in a Healthcare Setting: a Vision for the ClinGen Electronic Health Records Workgroup. Clin Pharmacol Ther. Feb. 2016;99(2):157-60.

\* cited by examiner

… (1)

GENERATING DATA IN STANDARDIZED FORMATS AND PROVIDING RECOMMENDATIONS

CROSS-REFERENCE TO RELATED APPLICATIONS

The instant application claims priority to U.S. Provisional Patent Application No. 62/686,383, titled "Method and Systems for Integrating Genomic Results with an Electronic Health Record" and filed Jun. 18, 2018, the disclosure of which is hereby incorporated by reference in its entirety.

STATEMENT OF FEDERAL FUNDING

This invention was made with government support under Grant Nos. 5U01HG006388 and 5U01HG008673 awarded by the National Institutes of Health. The government has certain rights in the invention.

TECHNICAL FIELD

Aspects of the present disclosure relate to medical data processing systems, and more specifically, systems for processing data to generate decisions and/or analytics for use in diagnosis and treatment.

BACKGROUND

Many healthcare institutions work with external laboratories for genetic and genomic testing. In a typical scenario, the external laboratories provide the genetic and/or genomic test results to a healthcare institution a non-computable format or hard-copy format, making the results unprocessable by the various computing systems that can exist within the healthcare institution. In the rare instance that the genetic and/or genomic test results are received electronically and in a computer-readable format, the results are typically structured in a way that prohibits existing systems from interpreting and processing the results, which makes it difficult for existing systems to automatically store and index the results for later retrieval and analysis.

SUMMARY

Systems and methods for integrating genomic results with electronic health records in accordance with embodiments of the invention are disclosed. In one embodiment, a method includes obtaining, by a computing device, first raw genetic data formatted in a first format, the first raw genetic data being associated with a patient, obtaining, by the computing device, second raw genetic data formatted in a second format, the second raw genetic data being associated with the patient, normalizing, by the computing device, the first raw genetic data by substituting at least one symbol in the first raw genetic data, normalizing, by the computing device, the second raw genetic data by substituting at least one symbol in the second raw genetic data, generating, by the computing device, genetic data for the patient by modifying the first raw genetic data by converting the normalized symbols in the first raw genetic data to a common format, modifying the second raw genetic data by converting the normalized symbols in the second raw genetic data to the common format, and generating the genetic data for the patient based on the first raw genetic data and the second raw genetic data, and storing, by the computing device, the genetic data such that the genetic data is immediately available to a plurality of devices.

In another embodiment of the invention, the method further includes generating a notification indicating a recommended treatment for the patient and transmitting the notification to a mobile device associated with a medical provider providing treatment to the patient.

In an additional embodiment of the invention, the method further includes administering the recommended treatment to the patient in a pharmacologically effective dose.

In yet another additional embodiment of the invention, the first format is incompatible with the second format.

In still another additional embodiment of the invention, the computing device stores the genetic data by transmitting the genetic data to an electronic health records system.

In yet still another additional embodiment of the invention, normalizing the first raw genetic data includes deleting at least one delimiter in the first raw genetic data.

In still another embodiment of the invention, converting the normalized symbols in the first raw genetic data to a common format includes converting a single nucleotide polymorphism to a pharmacogenetic star allele.

Yet another embodiment of the invention includes a data processing device including a processor, and a memory in communication with the processor and storing instructions, wherein the instructions, when read by the processor, cause the data processing device to obtain first raw genetic data formatted in a first format, the first raw genetic data being associated with a patient, obtain second raw genetic data formatted in a second format, the second raw genetic data being associated with the patient, normalize the first raw genetic data by substituting at least one symbol in the first raw genetic data, normalize the second raw genetic data by substituting at least one symbol in the second raw genetic data, generate genetic data for the patient by modifying the first raw genetic data by converting the normalized symbols in the first raw genetic data to a common format, modifying the second raw genetic data by converting the normalized symbols in the second raw genetic data to the common format, and generating the genetic data for the patient based on the first raw genetic data and the second raw genetic data, and store the genetic data such that the genetic data is immediately available to a plurality of devices.

In yet another additional embodiment of the invention, the instructions, when read by the processor, further cause the data processing device to generate a notification indicating a recommended treatment for the patient and transmit the notification to a mobile device associated with a medical provider providing treatment to the patient.

In still another additional embodiment of the invention, the notification causes an administering of the recommended treatment to the patient in a pharmacologically effective dose.

In yet still another additional embodiment of the invention, the first format is incompatible with the second format.

In still another embodiment of the invention, the instructions, when read by the processor, further cause the data processing device to store the genetic data by transmitting the genetic data to an electronic health records system.

In yet another embodiment of the invention, the instructions, when read by the processor, further cause the data processing device to normalize the first raw genetic data by deleting at least one delimiter in the first raw genetic data.

In yet still another embodiment of the invention, the instructions, when read by the processor, further cause the data processing device to convert the normalized symbols in the first raw genetic data to a common format by converting a single nucleotide polymorphism to a pharmacogenetic star allele.

Yet still another embodiment of the invention includes a non-transitory machine-readable medium storing instructions that, when executed by one or more processors, cause the one or more processors to perform steps including obtaining first raw genetic data formatted in a first format, the first raw genetic data being associated with a patient, obtaining second raw genetic data formatted in a second format, the second raw genetic data being associated with the patient, normalizing the first raw genetic data by substituting at least one symbol in the first raw genetic data, normalizing the second raw genetic data by substituting at least one symbol in the second raw genetic data, generating genetic data for the patient by modifying the first raw genetic data by converting the normalized symbols in the first raw genetic data to a common format, modifying the second raw genetic data by converting the normalized symbols in the second raw genetic data to the common format, and generating the genetic data for the patient based on the first raw genetic data and the second raw genetic data, and storing the genetic data such that the genetic data is immediately available to a plurality of devices.

In yet another additional embodiment of the invention, the instructions, when executed by one or more processors, further cause the one or more processors to perform steps including generating a notification indicating a recommended treatment for the patient and transmitting the notification to a mobile device associated with a medical provider providing treatment to the patient.

In still another additional embodiment of the invention, the first format is incompatible with the second format.

In yet still another additional embodiment of the invention, the instructions, when executed by one or more processors, further cause the one or more processors to perform steps including storing the genetic data by transmitting the genetic data to an electronic health records system.

In yet another embodiment of the invention, the instructions, when executed by one or more processors, further cause the one or more processors to perform steps including normalizing the first raw genetic data by deleting at least one delimiter in the first raw genetic data.

In still another embodiment of the invention, the instructions, when executed by one or more processors, further cause the one or more processors to perform steps including converting the normalized symbols in the first raw genetic data to a common format by converting a single nucleotide polymorphism to a pharmacogenetic star allele.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the claims.

BRIEF DESCRIPTION OF THE DRAWINGS

The description will be more fully understood with reference to the following figures, which are presented as exemplary embodiments of the invention and should not be construed as a complete recitation of the scope of the invention, wherein.

DETAILED DESCRIPTION

Figure 1:
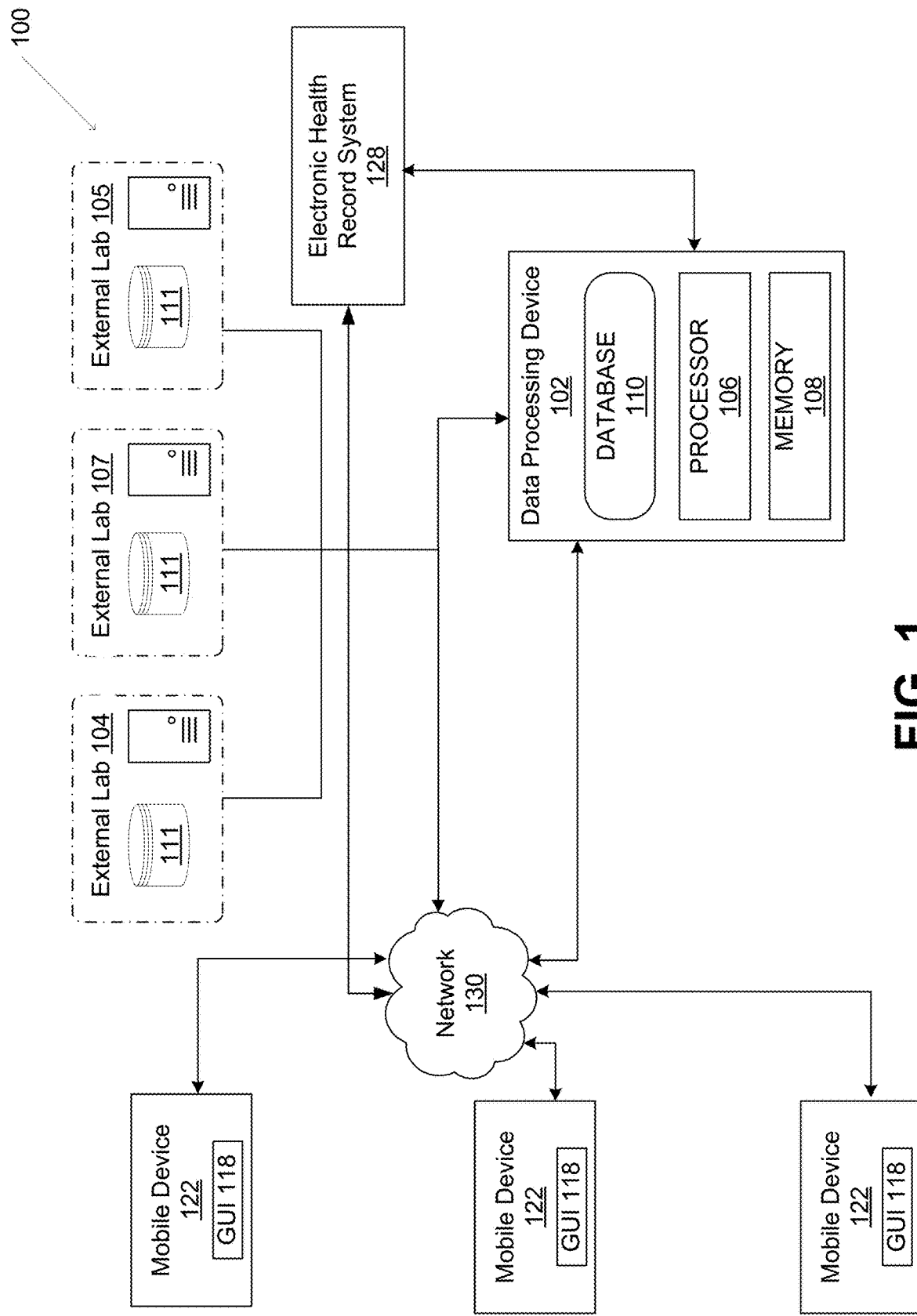
FIG. 1 is a block diagram illustrating a data processing system in accordance with an embodiment of the invention.

Turning now to the drawings, systems and methods for integrating genomic results with electronic health records in accordance with embodiments of the invention are disclosed. Many institutions have adopted genetic testing as part of clinical care, with some exploring how computable representations of genetic and genomic result data can facilitate clinical decision support. Genetic test results are typically provided as a plain-text representation of the interpretation report and transmitted using either the Health Level 7 version 2 standard or as files in the portable document format, both of which must be scanned from a fax or downloaded from an external laboratory portal before being manually integrated into an electronic health record system. Several national initiatives, including the "electronic health records and Genomics" (eMERGE) network, the "Clinical Sequencing Exploratory Research" (CSER) consortium, the "Implementing Genomics in Practice" (IG-NITE) network, and the "Displaying and Integrating Genetic Information Through the electronic health record system Action Collaborative" (DIGITizE) have proposed models for enabling more seamless integration of genetic and/or genomic result data with electronic health record system. For example, the eMERGE network proposed an omics ancillary system, which receives structured, computable results from a laboratory, stores the results in an optimized manner for processing (similar to a picture archiving and communications system for imaging), and returns actionable information to an electronic health record system. However, all of these tools and/or methodologies (including eMERGE) require a single laboratory source, and do not allow the direct transmission and integration of structured genetic results to the electronic health record system. Since many healthcare institutions work with several different third-party laboratories for genetic testing services, the ability to manage structured results from multiple and different external sources (e.g., multiple laboratories) is critical.

Data processing systems in accordance with embodiments of the invention solve these specific technical problems, among others, by automatically obtaining genetic and/or genomic data (collectively referred to herein as "genetic data") from multiple, disparate data sources (e.g., disparate data obtained from a single lab in multiple formats and/or data obtained from two separate labs in different formats), converting the data obtained from the disparate data sources into a common format (e.g. by generating structured genetic data), and storing the structured genetic data in a manner that allows the data to be processed and transmitted to existing electronic health record systems and/or otherwise integrated with existing electronic health record systems. Additionally, the data processing systems can obtain genetic data from multiple disparate data sources, such as laboratory computing systems, testing centers, and/or the like. The obtained data can be automatically transformed into structured data that represents only the most relevant genetic data and stores the structured data in a central repository. The data processing system can employ a rules engine to process the structured data to generate or otherwise predict a decision regarding the implication of the structured genetic data for use in clinical decision support.

In a variety of embodiments, graphical user interfaces can be provided by which a user, such as a health care provider or patient, is given remote access through the user interface to view or update the genetic information. Any updates to the data can first be converted into the standardized format and then stored in the collection of medical records on one or more of the network-based storage devices. In many embodiments, a notification can be automatically generated and transmitted based on data being loaded and/or modified in the system. This message can be transmitted in a standardized format so that all users can quickly be notified of any changes without having to manually look up or consolidate all of the updates. The message can be in the form of an email message, text message, or other type of message known in the art. The message can also indicate one or more treatment plans generated based on the genetic information. The treatment plans can be utilized to administer specific treatments to a patient in accordance with the particular patient's genetic profile.

Data Processing Systems

FIG. 1 illustrates one example of a data processing system 100 that can be used to implement various aspects of the present disclosure. The data processing system 100 includes various devices communicating and functioning together in the gathering, transmitting, and/or requesting data related to processing genetic data for integration with existing electronic health record system. Data processing system 100 includes a network 130 allows for communication between devices in the data processing system 100. The network 130 can include via one or more wireless networks such as, but not limited to one or more of a Local Area Network (LAN), Wireless Local Area Network (WLAN), a Personal Area Network (PAN), Campus Area Network (CAN), a Metropolitan Area Network (MAN), a Wide Area Network (WAN), a Wireless Wide Area Network (WWAN), Global System for Mobile Communications (GSM), Personal Communications Service (PCS), Digital Advanced Mobile Phone Service (D-Amps), Bluetooth, Wi-Fi, Fixed Wireless Data, 2G, 2.5G, 3G, 4G, LTE, and/or 5G networks, enhanced data rates for GSM evolution (EDGE), General packet radio service (GPRS), enhanced GPRS, messaging protocols such as, TCP/IP, SMS, MMS, extensible messaging and presence protocol (XMPP), real time messaging protocol (RTMP), instant messaging and presence protocol (IMPP), instant messaging, USSD, IRC, or any other wireless data networks or messaging protocols. Network 130 can also include wired networks and/or a combination of networks as appropriate.

The data processing system 100 includes a data processing device 102. Data processing device 102 includes a processor 106, a memory 108, and a database 110. The processor 106 can be directed by instructions stored in the memory 108 and/or database 110 to instruct the data processing device 102 to perform a variety of processes in accordance with embodiments of the invention, such as automatically acquiring, analyzing, and/or processing data received from one or more external labs 104, 105, 107. The data processing device 102 can obtain data, such as genetic data in a variety of incompatible formats, from the one or more external labs 104, 105, 107 and extract the most clinically relevant portions for storage in the database 110 in a standardized format. Given the standardized data, the data processing device 102 can predict or otherwise generate a decision (also referred to as an observation) that more describes the implication of any genetic and/or genomic variation identified in the genetic data. In several embodiments, the data processing device 102 may use a set of rules to process the genetic data and/or determine treatment recommendations. Accordingly, the data processing device 102 allows for genetic data provided, in differing formats, by the external laboratories 104, 105, and 107 to be searched, extracted, transmitted, stored, and/or processed in a common format by the data processing device 102.

The one or more external labs 104, 105, 107 can include various computing components and related systems that include or are otherwise capable of generating genetic data (e.g. genetic and/or genomic test results), such as scanners, control systems, departmental systems, and/or any other computing devices. The one or more external labs 104, 105, 107 can further include devices capable of generating image data (e.g., compressed and uncompressed image data) involving genetic data, data derived from such image data, data descriptive of system settings used to acquire the images, etc. In several embodiments, the one or more external labs 104, 105, 107 can include a genetic database 111. Such genetic databases 111 can include gene names, gene sequences, specific genetic markers and polymorphisms, as well as associations of such genetic information with specific individuals or populations.

An electronic health record system 128 can communicate with data processing device 102 to integrate genetic data within the electronic health record system. The electronic health record system 128 can include any computing device that collects and maintains a collection of patient health information in a particular format. Electronic health record system 128 stores electronic health records that include a range of data, such as demographical information, medical history, medication and allergies, immunization status, laboratory test results, radiology images, vital signs, personal statistics like age and weight, billing information, etc. The data processing device 102 can integrate with the electronic health record system 128 to provide data in a standardized format to the electronic health record system 128. Additionally, the data processing device 102 and/or mobile devices 122 can generate graphical-user interfaces at the electronic health record system 128 and/or dynamically drive existing functions of the electronic health record system 128 based on data received from the data processing device 102. Using data from the data processing device 102 to dynamically drive the prediction logic and graphical-user interfaces of the electronic health record system 128 allows the system to predict clinical observations, automatically and in real-time, and provide treatment recommendations which can be administered to patients. While the data processing system 100 only depicts one electronic health record system 128, it is contemplated that the data processing device 102 can interact with more than one electronic health record system.

One or more mobile devices 122 allows users, such as a clinician, to transmit data to and receive data from the data processing device 102 and/or electronic health record system 128. The one or more mobile devices 122 can be a personal computer, workstation, mobile phone, tablet device, and/or any other computing device capable of implementing and/or executing processes, software applications, etc. to perform any of a variety of processes as described herein. Mobile devices 122 can include one or more processors that process software or other machine-readable instructions and can include a memory to store the software or other machine-readable instructions and data. A mobile device 122 can also provide graphical user interface (GUI) 118 for obtaining data via network 130 and providing the GUI 118 for interacting with the obtained data and/or providing data to be processed by the data processing device 102 and/or electronic health record system 128. For example, genetic data and/or treatment recommendations can be displayed via the GUI 118. In several embodiments, a user interacts with the GUI 118 to initiate the processing of genetic data. In many embodiments, a user interacts with the GUI 118 to obtain treatment recommendations for a patient based on the genetic data associated with the patient.

Data processing systems and a variety of computing devices in accordance with embodiments of the invention are described above with respect to FIG. 1; however, it should be appreciated that any of a number of variations, such that those that utilize alternative networks and/or combinations of devices other than those specifically described, can be utilized in accordance with embodiments of the invention. In several embodiments, any device described herein can provide an interface, such as an application programming interface (API) or web service, which provides some or all of the data to for further processing. Access to the interface can be open and/or secured using any of a variety of techniques, such as by using client authorization keys, as appropriate to the requirements of specific applications of the invention.

Treatment Recommendations

Figure 2A:
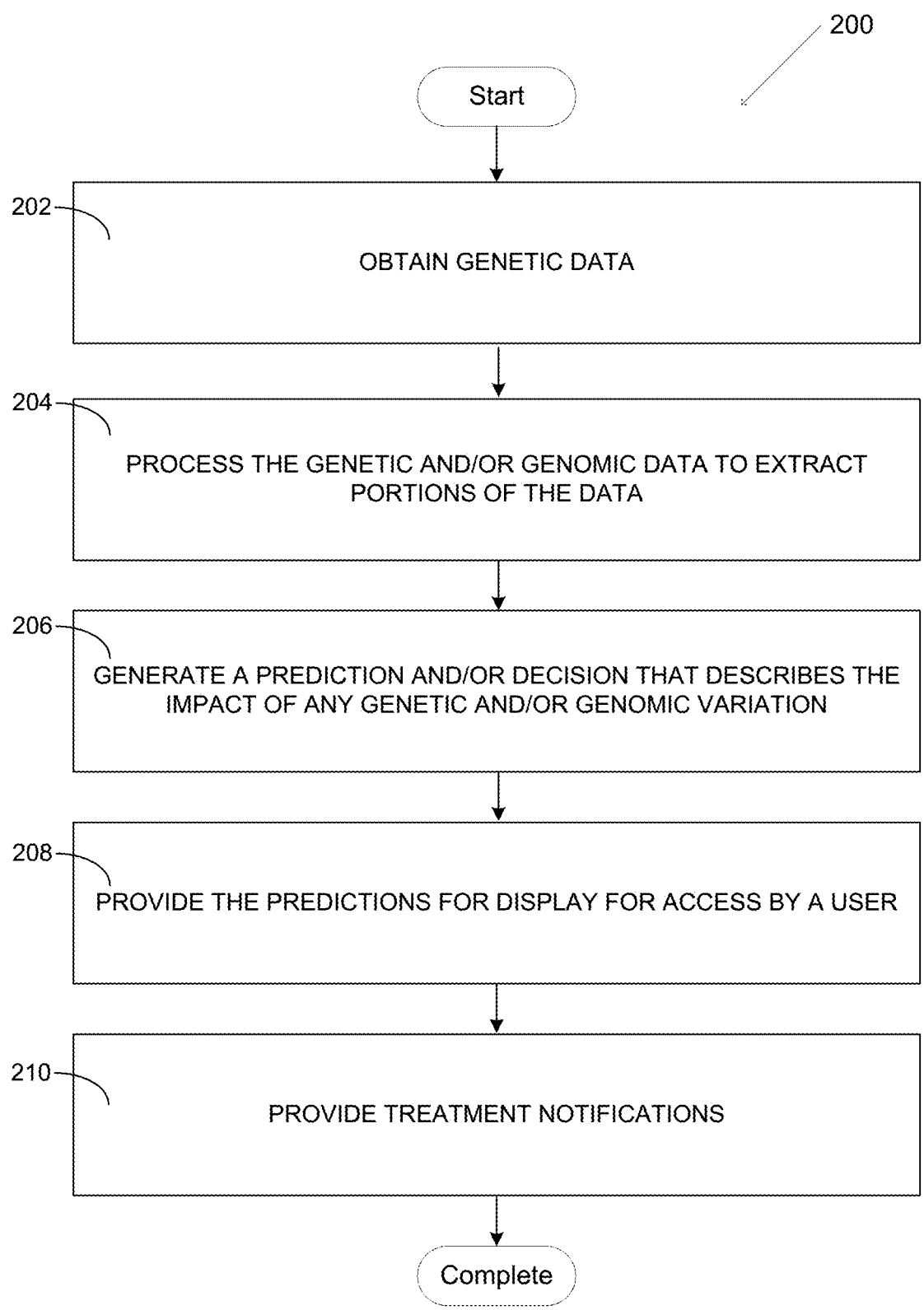
FIG. 2A is a flowchart of a process for providing treatment recommendations in accordance with an embodiment of the invention.

A variety of processes in accordance with embodiments of the invention include generating treatment recommendations (or other predictions) based on genetic data associated with a patient. The treatment recommendations can be provided to a medical provider who can administer treatments to the patient based on the patient's specific genomic information. Turning now to FIG. 2A, a process 200 for providing treatment recommendations in accordance with an embodiment of the invention is shown. Some or all of the steps of process 200 can be performed by any of the computing devices as described herein.

Genetic data can be obtained (202). In several embodiments, the genetic data can be obtained from two or more disparate data sources, such as one or more external laboratories. The genetic data can be provided in any format. Typically, the genetic data is provided in a format that is specific to the data source providing the genetic data. That is, the format of genetic data provided by a first data source is typically incompatible with the format of genetic data provided by a second data source. Genetic data can include any data indicating the genetic characteristics of a patient as described herein.

The genetic data can be processed (204) to extract portions of the data. In a variety of embodiments, the extracted portions of data include data elements that are known to be used and/or anticipated to be used in determining a treatment recommendation for a particular patient. As additional genetic data is provided by a laboratory, and/or as the knowledge available to generate treatment recommendations and diagnoses based on new scientific discoveries and clinical evidence, additional data elements can also be extracted from the genetic data. This can improve the performance of the computing device by reducing the amount of data to be processed. A variety of processes that can be used to process genetic data are described in more detail with respect to FIG. 2B. In many embodiments, the processed genetic data is stored in a database in a standardized format, such as a database provided by an electronic health records system. For example, the processed genetic data can be stored in an entity-attribute-value format within a relational database. In a variety of embodiments, the standardized format used to represent the genetic data can be based on the specific formats in which raw genetic data is provided.

The processed genetic data can be used to generate (206) a prediction and/or decision that describes the impact of any genetic variation in the processed genetic data. In a number of embodiments, the prediction and/or decision can include treatment recommendations for treating a patient associated with the genetic data. For example, the processed genetic data can include single nucleotide polymorphisms ("SNPs") (such as SLCO1B1/simvastatin and/or VKORC1/warfarin) and/or star variants (such as CYP2C19/clopidogrel and/or CYP2C9/warfarin). A treatment plan can be determined based on the particular SNPs present in the processed genetic data. In several embodiments, a treatment plan can be developed based on existing treatment recommendations, such as those provided by the Clinical Pharmacogenetics Implementation Consortium. In many embodiments, if a treatment plan cannot be determined, a notification can be generated that indicates that the case should be reviewed and/or subject to further processing and analysis.

The generated predictions and/or treatment recommendations can be provided (210). In several embodiments, the generated predictions are provided to a computing device associated with a medical provider, where the computing device can provide a graphical user interface for presenting the treatment recommendations. In a number of embodiments, providing (210) predictions and/or treatment recommendations includes encapsulating the predictions and/or recommendation into an instruction (and/or notification) and transmitting the instruction to an external computing system, such as an electronic health record system. The instructions can cause the external computing system to perform one or more functions. In several embodiments, the instruction causes the generated predictions and/or treatment recommendations to be shared in a standardized format interpretable by a variety of electronic health record systems. For example, the predictions can be transmitted using a HL7v2 interface. Based on the presented treatment recommendations, the medical provider can administer the appropriate treatment to the patient. For example, if the genetic data indicates that a SNP in SLCO1B1 is present in a patient's genetic data, the drug simvastatin can be administered to the patient in a pharmacologically effective dose determined based on the genetic data. Similarly, any other drug can be administered to a patient based on particular indications in the genetic data in a pharmacologically effective amount determined based on the genetic data.

Specific processes for the generation of treatment recommendations based on standardized data in accordance with embodiments of the invention are described with respect to FIG. 2A; however, any of variety of processes, including those that provide alternative mechanisms for providing treatment recommendations, can be utilized as appropriate to the requirements of specific applications of embodiments of the invention.

Generating Standardized Data

Many processes in accordance with embodiments of the invention include obtaining genetic data from multiple, disparate data sources in differing formats and converting the obtained genetic data into a common format. The genetic data, once processed into a common format, can be easily stored by a variety of computing systems and/or used to generate treatment recommendations. Turning now to FIG.

2B, a process 250 for generating genetic data in a standardized format in accordance with an embodiment of the invention is shown. Some or all of the steps of process 250 can be performed by any of the computing devices as described herein.

Raw data can be obtained (252). The raw data can include raw genetic data obtained from multiple data sources and can be in a variety of incompatible formats as described herein.

Data types for the raw genetic data can be determined (254). Data types within the raw genetic data can include a variety of characters representing underlying genetic and/or genomic data along with a variety of symbols, such as delimiters indicating structure within the characters and within the raw genetic data, in a particular format. The particular characters and symbols used to represent a particular concept in the raw data can be dependent on the particular format used to encode the raw data. In a variety of embodiments, the raw data includes single nucleotide polymorphisms (SNPs) for a patient. SNPs represent the most common type of genetic variation among people, with each SNP representing a difference in a single DNA building block, called a nucleotide. For example, a SNP can replace the nucleotide cytosine (C) with the nucleotide thymine (T) in a certain stretch of DNA.

Figure 3:
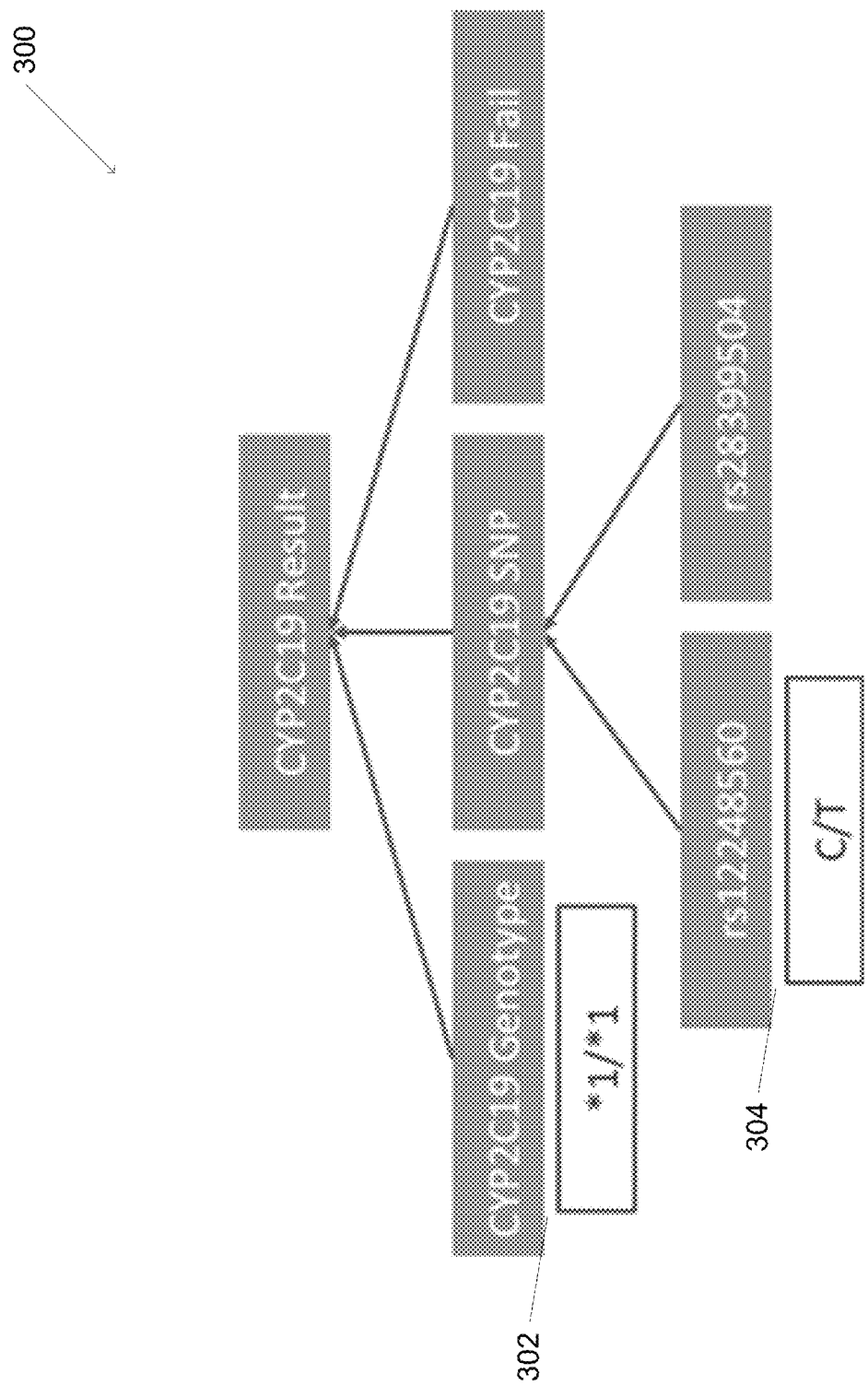
FIG. 3 is a block diagram illustrating a hierarchical classification in accordance with an embodiment of the invention.

The raw genetic data can be normalized (256). Normalizing the raw genetic data can include eliminating and/or substituting particular symbols within the raw genetic data. The particular substitutions and/or deletions of symbols can be based on the particular format used to encode the raw genetic data. For example, for any values in the raw genetic data that are SNPs, normalizing the raw genetic data can be performed by translating particular sequences of characters in the raw genetic data to a result in a standardized format (e.g., a single T can be normalized as TT). In many embodiments, delimiter characters are removed to produce the normalized result (e.g., G/G can be normalized to GG). In several embodiments, a hierarchical classification can be used to normalize raw genetic data into a standardized format. Turning now to FIG. 3, a hierarchical classification 300 in accordance with an embodiment of the invention is shown. The hierarchical classification 300 shows a classification for the gene CYP2C19, with results being classified as being a genotype result, such as result 302 and/or as an individual SNP classified with specific sequence identifier (e.g. a "rs number"), such as SNP 304. The use of a hierarchical classification allows for a computationally efficient normalization of raw genetic data into a standardized format. As shown in hierarchical classification 300, a normalization for CYP2C19 results expressed in the raw genetic data could be normalized into standardized genotype and SNP results.

If abnormal data is present (258), errors in the raw genetic data can be corrected (260). Abnormal data in the raw genetic data can include any characters and/or symbols that cannot be converted into a standardized format. Correcting errors in the raw genetic data can include deleting erroneous data from the raw genetic data and/or replacing erroneous data with known good data. In many embodiments, correction codes can be applied to the raw genetic data in order to correct common transcription errors, particularly those present in the identification of SNPs in particular genetic results. For example, if the normalization of the raw genetic data does not result in of two of the four possible characters (A, C, G, T) that can be used in a SNP, the result can be flagged as having abnormal data. The abnormal data and corresponding raw genetic data can be processed to determine potential errors in the raw genetic data and/or normalization processes. In many embodiments, a machine classifier can be used to automatically identify and correct errors and/or calculate a probabilistic likelihood that an error has been corrected. Any of a variety of machine classifiers can be utilized including (but not limited to) decision trees, k-nearest neighbors, support vector machines (SVM), neural networks (NN), recurrent neural networks (RNN), convolutional neural networks (CNN), and/or probabilistic neural networks (PNN). RNNs can further include (but are not limited to) fully recurrent networks, Hopfield networks, Boltzmann machines, self-organizing maps, learning vector quantization, simple recurrent networks, echo state networks, long short-term memory networks, bi-directional RNNs, hierarchical RNNs, stochastic neural networks, and/or genetic scale RNNs. In some embodiments of the invention, any of a variety of processes described herein can be used to train the machine classifier. In a number of embodiments, a combination of machine classifiers can be utilized, more specific machine classifiers when available, and general machine classifiers at other times can further increase the accuracy of corrections. Once the data errors are corrected (260), the corrected data can be normalized (256).

When abnormal data is not present (258) in the normalized data, genetic data in a standardized format can be generated (262). In a variety of embodiments, SNPs can be converted to pharmacogenetic star alleles in a standardized format. In a number of embodiments, if no pharmacogenetic star alleles correspond to a normalized SNPs, a default value (such as *1/*1, also known as a wild type) can be used. In several embodiments, if one star allele corresponds to a normalized SNP, the result can be determined to be heterogeneous and one default value added (e.g., *2→*1/*2). In a variety of embodiments, if two star alleles correspond to a normalized SNP, the two star alleles can be used without substation or modification. In many embodiments, the star alleles can be normalized to remove all unnecessary characters and delimiters, such as removing all symbols except asterisks and numeric values. The standardized genetic data can be stored and/or processed as described herein.

In many embodiments, multiple pieces of raw genetic data for a particular patient can be provided, at least two of the pieces of raw genetic data being formatted using different formats. Each piece of raw genetic data can be processed and converted into a standardized format as describe herein, and each piece of standardized genetic data for the patient can be combined into a single piece of genetic data that can be stored and/or used to generate treatment recommendations for the patient as described herein.

Figure 2B:
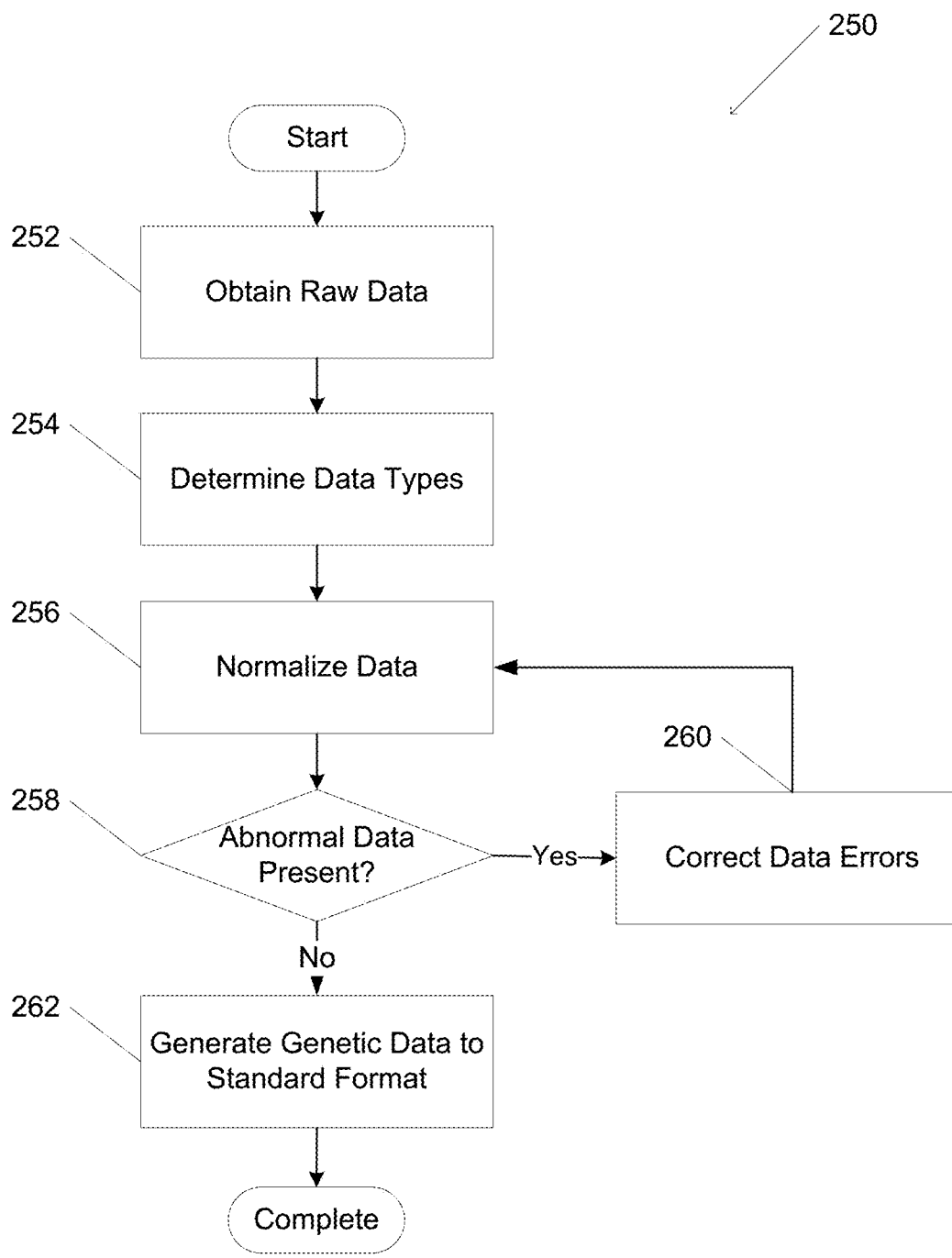
FIG. 2B is a flowchart of a process for generating data in a standardized format in accordance with an embodiment of the invention.

Specific processes for the generation of genetic data in standardized formats and classification schemes in accordance with embodiments of the invention are described with respect to FIGS. 2B and 3; however, any of variety of processes, including those that utilize alternative criteria for normalizing raw data and/or correcting errors in the data, can be utilized as appropriate to the requirements of specific applications of embodiments of the invention.

Computing Devices

Figure 4:
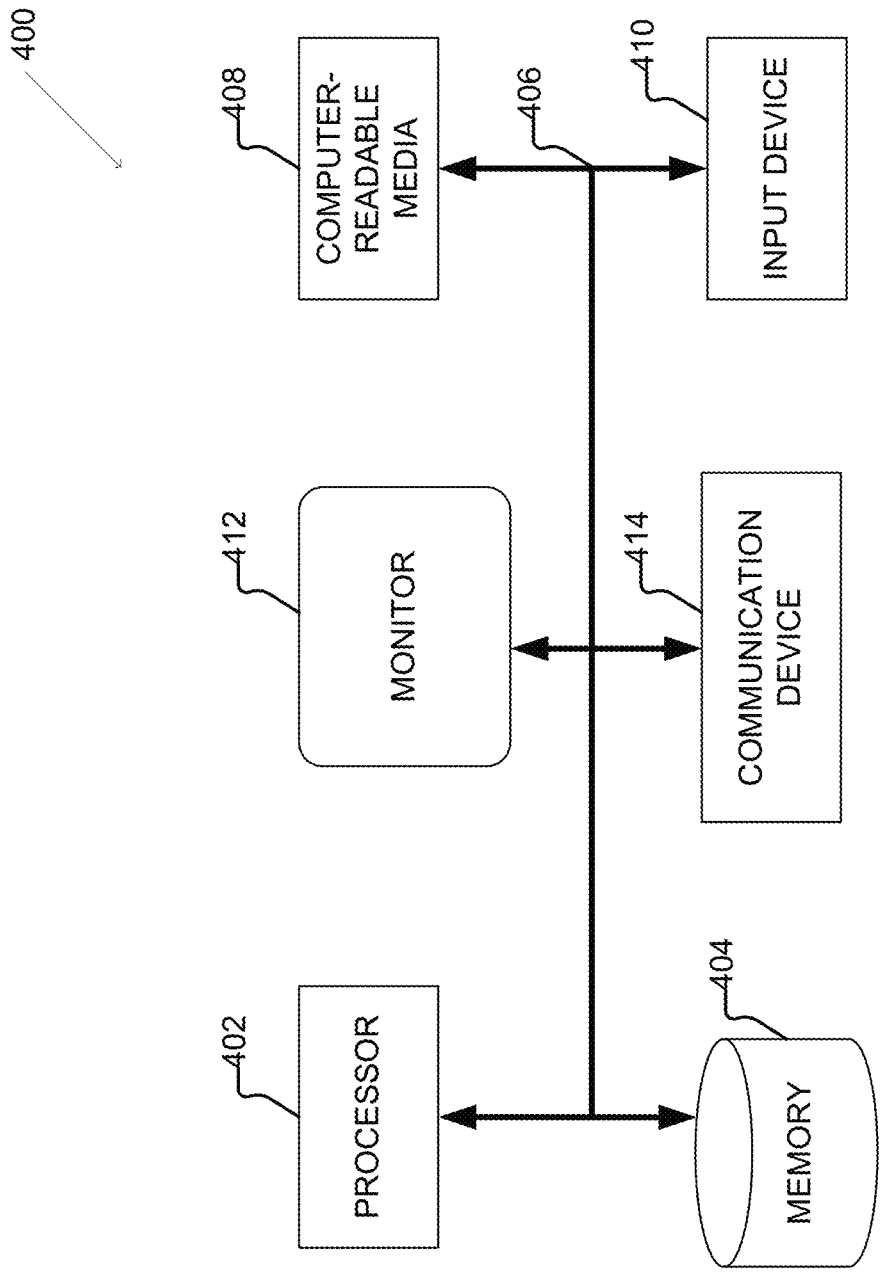
FIG. 4 is a block diagram illustrating a computing device in accordance with an embodiment of the invention.

FIG. 4 illustrates an example of a computing device 400 that can be used to implement any of the various devices described herein such as, but not limited to, data processing device 102, electronic health record system 128, mobile device 122, and/or external lab 104, 105, 107 as described with respect to FIG. 1. Computing device 400 can include personal computers, server computers, hand-held or laptop devices, tablet devices, multiprocessor systems, microprocessor-based systems, set top boxes, programmable consumer electronic devices, network PCs, minicomputers, mainframe computers, digital signal processors, state machines, logic circuitries, distributed computing environments that include any of the above computing systems or devices, and the like.

Computing device 400 can include various hardware components, such as one or more processors 402, memory 404, and a system bus 406 that couples components of the computing device 400 to the processors 402. The system bus 406 can be any of several types of bus structures including a memory bus, memory controller, a peripheral bus, and/or a local bus using any of a variety of bus architectures.

The computer 400 can further include a variety of computer-readable media 408 that includes removable/non-removable media and volatile/nonvolatile media. Computer-readable media 408 can also include computer storage media and communication media. Computer storage media includes removable and/or non-removable media and volatile and/or nonvolatile media implemented in any method or technology for storage of information, such as computer-readable instructions, data structures, program modules or other data, such as RAM, ROM, EEPROM, flash memory or other memory technology, CD-ROM, digital versatile disks (DVD) or other optical disk storage, magnetic cassettes, magnetic tape, magnetic disk storage or other magnetic storage devices, and/or any other medium that can be used to store the desired information/data and which can be accessed by the computing device 400. Communication media includes computer-readable instructions, data structures, program modules, or other data in a modulated data signal such as a carrier wave or other transport mechanism and includes any information delivery media. For example, communication media can include wired media such as a wired network or direct-wired connection and wireless media such as acoustic, RF, infrared, and/or other wireless media, or some combination thereof. Computer-readable media can be embodied as a computer program product, such as software stored on computer storage media.

Memory 404 includes computer storage media in the form of volatile/nonvolatile memory such as read only memory (ROM) and random access memory (RAM). A basic input/output system (BIOS), containing the basic routines that help to transfer information between elements within the computing device 400 (e.g., during start-up) is typically stored in ROM. RAM typically contains data and/or program modules that are immediately accessible to and/or presently being operated on by processors 402. In many embodiments, memory 404 holds an operating system, application programs, and other program modules and program data that, when read by processors 402, cause the computing device 400 to perform any processes, or combinations thereof, as described herein. Memory 404 can also include other removable, non-removable, volatile, and/or nonvolatile computer storage media. For example, memory 404 can include a hard disk drive that reads from or writes to non-removable, nonvolatile magnetic media, a magnetic disk drive that reads from or writes to a removable, nonvolatile magnetic disk, and/or an optical disk drive that reads from or writes to a removable, nonvolatile optical disk such as a CD-ROM or other optical media. Other removable, non-removable, volatile, and/or nonvolatile computer storage media can include magnetic tape cassettes, flash memory cards, digital versatile disks, digital video tape, solid state RAM, solid state ROM, and the like.

Input data, such as commands and information, can be obtained using one or more input devices 410. Input device 410 can include a variety of devices such as, but not limited to, touch screen interfaces, electronic digitizers, microphones, keyboards, and/or pointing devices such as mice, trackballs, and/or touch pads. Other input devices can include joysticks, game pads, satellite dishes, scanners, and/or the like. Voice inputs, gesture inputs, and/or other natural user interfaces can also be used with the appropriate input devices 410, such as microphones, cameras, touch screen interfaces, gloves, and/or any other sensor. Input devices 410 can be coupled to the processor 402 via system bus 406 and/or memory 404, but can be connected by other interface and bus structures, such as a parallel port, game port, and/or a universal serial bus as appropriate. A monitor 412, or other type of display device, can also be connected to the system bus 406 via an interface, such as a video interface. The monitor 412 can also be integrated with an input device, such as a touchscreen interface.

The computing device 400 can operate in a networked or cloud-computing environment using communications device 414 to communicate with one or more remote devices, such as a remote computer, via any network as described herein. When used in a networked or cloud-computing environment, the computing device 400 can be connected to a public and/or private network through the communication device 414. In several embodiments, communication device 414 includes a modem or other means for establishing communications over a network. In a number of embodiments, any data described herein can be stored using a device remote from the computing device 400 and obtained by the computing device 400 using the communication device 414.

Although specific architectures for computing devices in accordance with embodiments of the invention are conceptually illustrated in FIG. 4, any of a variety of architectures, including those that store data or applications on disk or some other form of storage and are loaded into memory at runtime, can also be utilized. Additionally, any of the data utilized in a computing device can be cached and transmitted once a network connection (such as a wireless network connection via the communications interface) becomes available. In a variety of embodiments, a memory includes circuitry such as, but not limited to, memory cells constructed using transistors, that store instructions. Similarly, a processor can include logic gates formed from transistors (or any other device) that dynamically perform actions based on the instructions stored in the memory. In several embodiments, the instructions are embodied in a configuration of logic gates within the processor to implement and/or perform actions described by the instructions. In this way, the systems and methods described herein can be performed utilizing both general-purpose computing hardware and by single-purpose devices.

Although the present invention has been described in certain specific aspects, many additional modifications and variations would be apparent to those skilled in the art.

In particular, any of the various processes described above can be performed in alternative sequences and/or in parallel (on the same or on different computing devices) in order to achieve similar results in a manner that is more appropriate to the requirements of a specific application. It is therefore to be understood that the present invention can be practiced otherwise than specifically described without departing from the scope and spirit of the present invention. Thus, embodiments of the present invention should be considered in all respects as illustrative and not restrictive. It will be evident to the annotator skilled in the art to freely combine several or all of the embodiments discussed here as deemed suitable for a specific application of the invention. Throughout this disclosure, terms like "advantageous", "exemplary" or "preferred" indicate elements or dimensions which are particularly suitable (but not essential) to the invention or an embodiment thereof, and can be modified wherever deemed suitable by the skilled annotator, except where expressly required. Accordingly, the scope of the invention should be determined not by the embodiments illustrated, but by the appended claims and their equivalents.

What is claimed is:

1. A method comprising:
   obtaining, by a computing device from a first data source, first raw genetic data formatted in a first format, the first raw genetic data being associated with a patient;
   obtaining, by the computing device from a second data source, second raw genetic data formatted in a second format, the second raw genetic data being associated with the patient;
   normalizing, by the computing device, a first character sequence of the first raw genetic data by substituting at least one symbol in the first raw genetic data;
   normalizing, by the computing device, a second character sequence of the second raw genetic data by substituting at least one symbol in the second raw genetic data;
   generating, by the computing device, genetic data for the patient by:
      modifying the first raw genetic data by converting the normalized symbols in the first raw genetic data to a common format;
      modifying the second raw genetic data by converting the normalized symbols in the second raw genetic data to the common format; and
      generating the genetic data for the patient based on the first raw genetic data and the second raw genetic data;
   communicating the genetic data to a plurality of devices by storing, by the computing device, the genetic data in an electronic health record associated with the patient, wherein the genetic data is immediately available to the plurality of devices via the electronic health record;
   generating, in real time, a notification comprising the genetic data and indicating a recommended treatment for the patient; and
   causing presentation of the notification via a user interface of a mobile device associated with a medical provider providing the recommended treatment to the patient based on the patient's specific genomic information comprising the genetic data.

2. The method of claim 1, further comprising:
   causing generation, at a user device, a graphical user interface comprising a visual representation of at least one of the first raw genetic data or the second raw genetic data, and an input to initiate processing of at least one of the first raw genetic data and the second raw genetic data; and
   initiating, by the computing device and based on receipt of the input to initiate the processing, real-time generation of the genetic data of the patient.

3. The method of claim 2, further comprising administering the recommended treatment to the patient in a pharmacologically effective dose.

4. The method of claim 1, wherein the first format is incompatible with the second format.

5. The method of claim 1, wherein the computing device stores the genetic data by transmitting the genetic data to an electronic health records system.

6. The method of claim 1, wherein normalizing the first raw genetic data comprises deleting at least one delimiter in the first raw genetic data.

7. The method of claim 1, wherein converting the normalized symbols in the first raw genetic data to a common format comprises converting a single nucleotide polymorphism to a pharmacogenetic star allele.

8. A data processing device, comprising:
   a processor; and
   a memory in communication with the processor and storing instructions;
   wherein the instructions, when read by the processor, cause the data processing device to:
      obtain, via a network and from a first data source, first raw genetic data formatted in a first format, the first raw genetic data being associated with a patient;
      obtain, via a network and from a second data source, second raw genetic data formatted in a second format, the second raw genetic data being associated with the patient;
      normalize a first character sequence of the first raw genetic data by substituting at least one symbol in the first raw genetic data;
      normalize a second character sequence of the second raw genetic data by substituting at least one symbol in the second raw genetic data;
      generate genetic data for the patient by:
         modifying the first raw genetic data by converting the normalized symbols in the first raw genetic data to a common format;
         modifying the second raw genetic data by converting the normalized symbols in the second raw genetic data to the common format; and
         generating the genetic data for the patient based on the first raw genetic data and the second raw genetic data;
      communicating the genetic data to a plurality of devices by storing, via a network and in a data store, the genetic data in an electronic health record associated with the patient, wherein the genetic data is immediately available to the plurality of devices;
      automatically generating a real-time notification comprising the genetic data and indicating a recommended treatment for the patient; and
      causing presentation of the notification via a user interface of a mobile device associated with a medical provider providing the recommended treatment to the patient based on presentation of the patient's specific genomic information comprising the genetic data.

9. The data processing device of claim 8, wherein the instructions, when read by the processor, further cause the data processing device to:
   cause generation, at a user device, a graphical user interface comprising a visual representation of at least one of the first raw genetic data or the second raw genetic data, and an input to initiate processing of at least one of the first raw genetic data and the second raw genetic data; and
   initiate, based on receipt of the input from the user device, generation of the genetic data of the patient in real-time.

10. The data processing device of claim 9, wherein the notification causes an administering of the recommended treatment to the patient in a pharmacologically effective dose.

11. The data processing device of claim 8, wherein the first format is incompatible with the second format.

12. The data processing device of claim 8, wherein automatic generation of the notification is based on the storing of the genetic data and wherein the instructions, when read by the processor, further cause the data processing device to store the genetic data by transmitting the genetic data to an electronic health records system.

13. The data processing device of claim 8, wherein the instructions, when read by the processor, further cause the data processing device to normalize the first raw genetic data by deleting at least one delimiter in the first raw genetic data.

14. The data processing device of claim 8, wherein the instructions, when read by the processor, further cause the data processing device to convert the normalized symbols in the first raw genetic data to a common format by converting a single nucleotide polymorphism to a pharmacogenetic star allele.

15. A non-transitory machine-readable medium storing instructions that, when executed by one or more processors, cause the one or more processors to perform steps comprising:
   obtaining, from a first data source stored on a first laboratory computing system, first raw genetic data formatted in a first format, the first raw genetic data being associated with a patient;
   obtaining, from a second data source stored on a second laboratory computing system, second raw genetic data formatted in a second format, the second raw genetic data being associated with the patient;
   normalizing a first character sequence of the first raw genetic data by substituting at least one symbol in the first raw genetic data;
   normalizing a second character sequence of the second raw genetic data by the second raw genetic data using hierarchical classification;
   generating genetic data for the patient by:
      modifying the first raw genetic data by converting the normalized symbols in the first raw genetic data to a common format;
      modifying the second raw genetic data by converting the normalized symbols in the second raw genetic data to the common format;
      generating the genetic data for the patient based on the first raw genetic data and the second raw genetic data; and
   communicating the genetic data to a plurality of devices by storing, in a data store of an electronic health record system, the genetic data in an electronic health record associated with the patient, wherein the genetic data is immediately available to the plurality of devices via the electronic health record;
   generating a real-time notification comprising the genetic data and a notification indicating a recommended treatment for the patient; and
   causing presentation of the notification via a user interface of a mobile device associated with a medical provider providing the recommended treatment to the patient based on the patient's specific genomic information comprising the genetic data.

16. The non-transitory machine-readable medium of claim 15, wherein the instructions, when executed by one or more processors, further cause the one or more processors to perform steps comprising:
   causing generation, at a user device, a graphical, user interface comprising a visual representation of at least one of the first raw genetic data or the second raw genetic data, and an input to initiate processing of at least one of the first raw genetic data and the second raw genetic data; and
   initiating, by the one or more processors and based on receipt of the input to initiate the processing, real-time generation of the genetic data of the patient.

17. The non-transitory machine-readable medium of claim 15, wherein the first format is incompatible with the second format.

18. The non-transitory machine-readable medium of claim 15, wherein the instructions, when executed by one or more processors, further cause the one or more processors to perform steps comprising storing the genetic data by transmitting the genetic data to the electronic health records system.

19. The non-transitory machine-readable medium of claim 15, wherein the instructions, when executed by one or more processors, further cause the one or more processors to perform steps comprising normalizing the first raw genetic data by deleting at least one delimiter in the first raw genetic data.

20. The non-transitory machine-readable medium of claim 15, wherein the instructions, when executed by one or more processors, further cause the one or more processors to perform steps comprising converting the normalized symbols in the first raw genetic data to a common format by converting a single nucleotide polymorphism to a pharmacogenetic star allele.

* * * * *